US009968326B2

(12) United States Patent
Kobayashi et al.

(10) Patent No.: US 9,968,326 B2
(45) Date of Patent: May 15, 2018

(54) X-RAY DIAGNOSTIC APPARATUS

(71) Applicant: Toshiba Medical Systems Corporation, Otawara-shi (JP)

(72) Inventors: Yoshimasa Kobayashi, Nasushiobara (JP); Shumpei Ohashi, Otawara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 229 days.

(21) Appl. No.: 14/794,161

(22) Filed: Jul. 8, 2015

(65) Prior Publication Data

US 2016/0007949 A1 Jan. 14, 2016

(30) Foreign Application Priority Data

Jul. 9, 2014 (JP) ................................ 2014-141781

(51) Int. Cl.

| | |
|---|---|
| ***H05G 1/06*** | (2006.01) |
| ***A61B 6/00*** | (2006.01) |
| ***H01J 35/16*** | (2006.01) |
| ***H01J 35/02*** | (2006.01) |

(52) U.S. Cl.

CPC .................. *A61B 6/54* (2013.01); *A61B 6/40* (2013.01); *A61B 6/4441* (2013.01); *A61B 6/4452* (2013.01); *A61B 6/4482* (2013.01); *A61B 6/4488* (2013.01); *A61B 6/504* (2013.01); *H01J 35/025* (2013.01); *H01J 35/16* (2013.01); *A61B 6/487* (2013.01); *A61B 6/5205* (2013.01); *A61B 6/582* (2013.01); *H01J 2235/1216* (2013.01); *H01J 2235/162* (2013.01)

(58) Field of Classification Search

CPC ... A61B 6/4441; A61B 6/4405; A61B 6/4464; A61B 6/032; A61B 6/4458; A61B 6/4452; A61B 6/4476; A61B 6/547; A61B 6/4233; A61B 6/587; A61B 6/04; A61B 6/102; A61B 6/504; A61B 6/027; A61B 6/4435; A61B 6/545; A61B 6/548; A61B 6/40; A61B 6/4482; A61B 6/4488; A61B 6/487; A61B 6/5205; A61B 6/54; A61B 6/582; H01J 2235/1216; H01J 2235/162; H01J 35/025; H01J 35/16

USPC ................................ 378/4, 15, 62, 193–200

See application file for complete search history.

(56) References Cited

U.S. PATENT DOCUMENTS 6,142,667 A * 11/2000 Pattee ................. A61B 6/4405 378/197

7,985,023 B2 7/2011 Gross et al.

(Continued)

*Primary Examiner* — Irakli Kiknadze

(74) *Attorney, Agent, or Firm* — Oblon, McClelland, Maier & Neustadt, L.L.P.

(57) ABSTRACT

An X-ray diagnostic apparatus according to an embodiment includes an X-ray tube holding device, an X-ray detector, a rotator, an arm, and a tubular body. The X-ray tube holding device generates X-rays. The X-ray detector detects the X-rays. The rotator holds the X-ray tube holding device so as to be rotatable about a first rotation axis obtained by setting an irradiation direction of the X-rays as an axis. The arm holds the rotator and the X-ray detector and is rotatable about a second rotation axis different from the first rotation axis. The tubular body connects the X-ray tube holding device and a device away from the arm. The arm holds the rotator so as to be rotatable about the first rotation axis in a direction in which torsion of the tubular body is reduced.

11 Claims, 14 Drawing Sheets

(56) References Cited

U.S. PATENT DOCUMENTS

| | | | | |
|---|---|---|---|---|
| 2008/0119714 | A1* | 5/2008 | Meissner | A61B 6/032 600/407 |
| 2011/0013742 | A1* | 1/2011 | Zaiki | A61B 6/035 378/15 |
| 2012/0085078 | A1* | 4/2012 | Rijken | H02G 3/0475 59/78.1 |
| 2012/0275571 | A1 | 11/2012 | Neuber | |
| 2013/0202093 | A1* | 8/2013 | Meyer | H05G 1/02 378/197 |

* cited by examiner

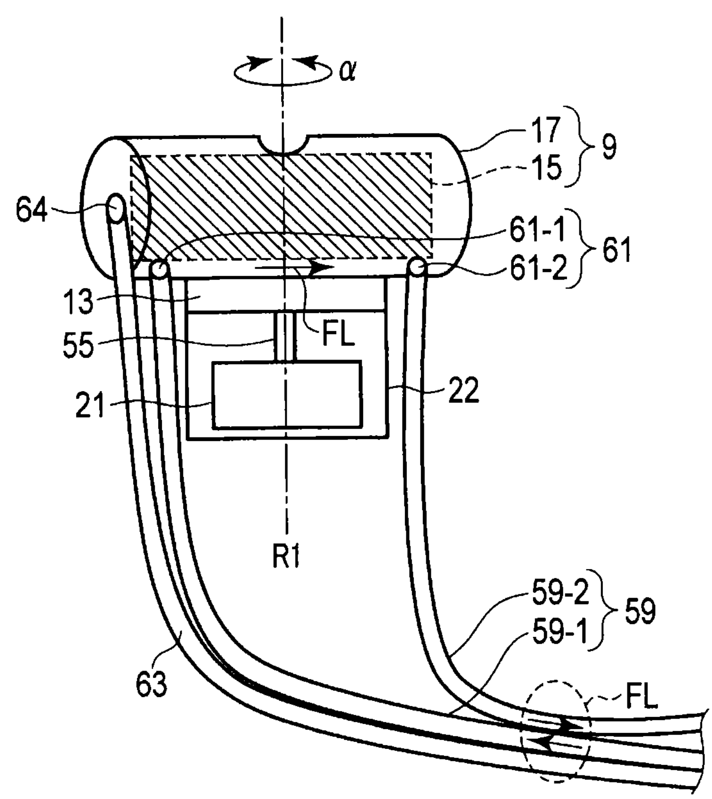
F I G. 3

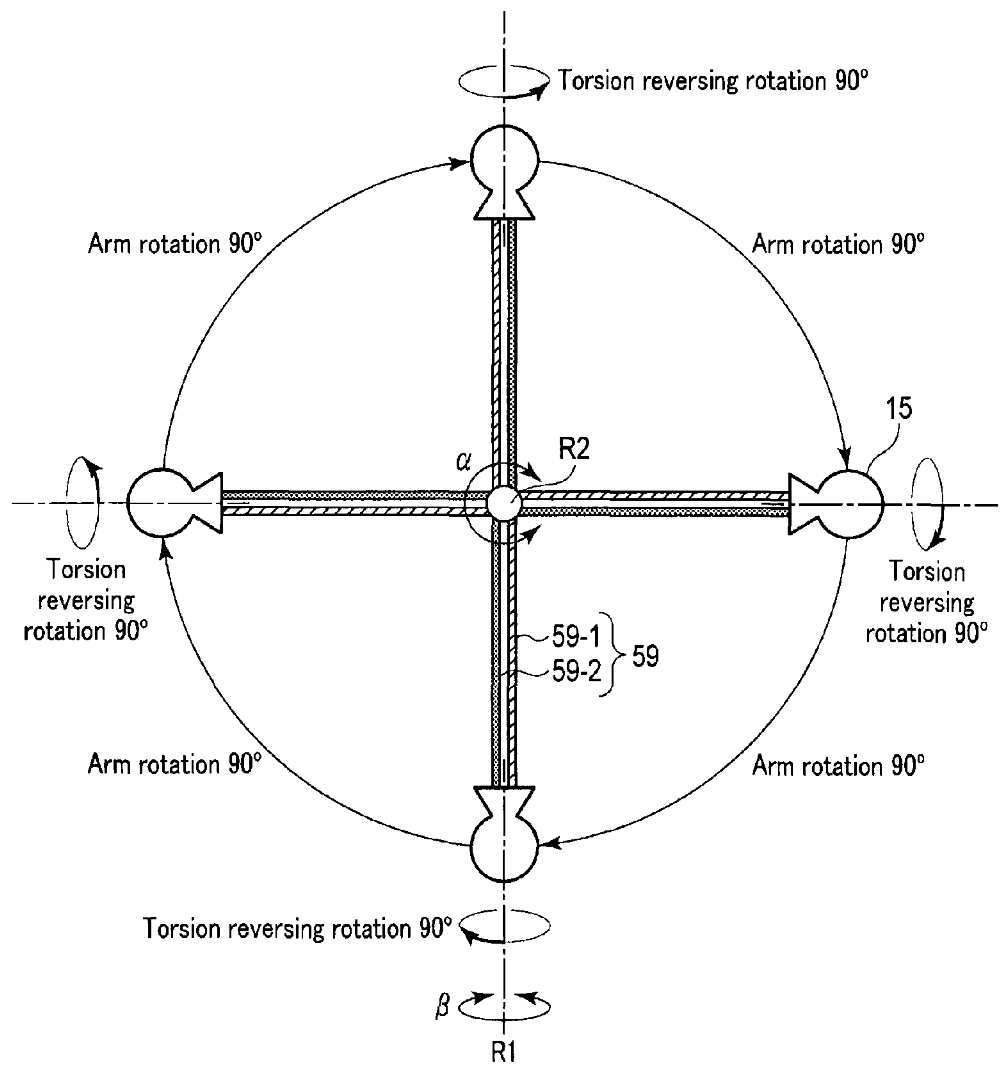
F I G. 4

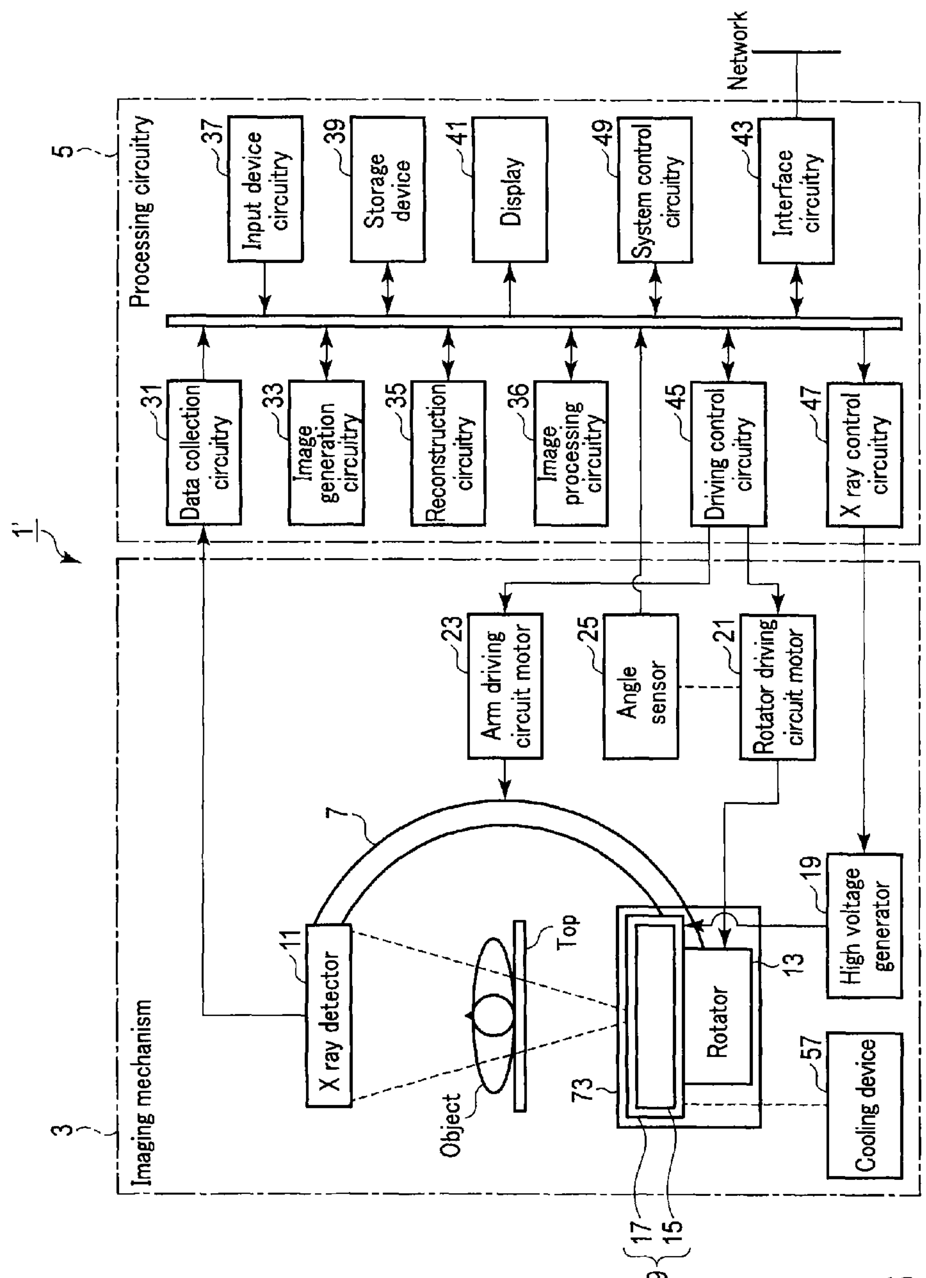
F I G. 6

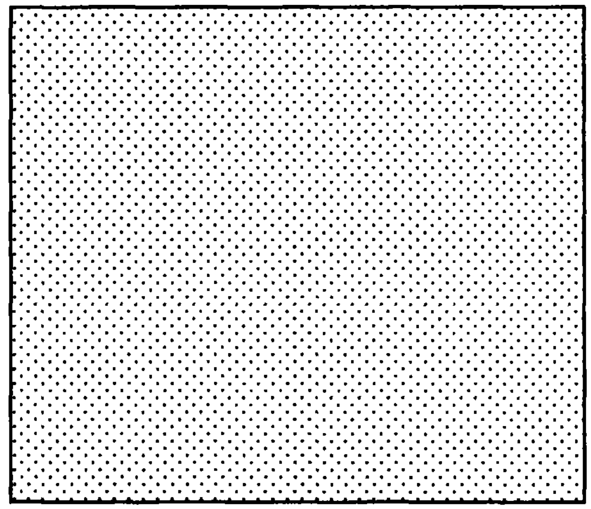
F I G. 8B
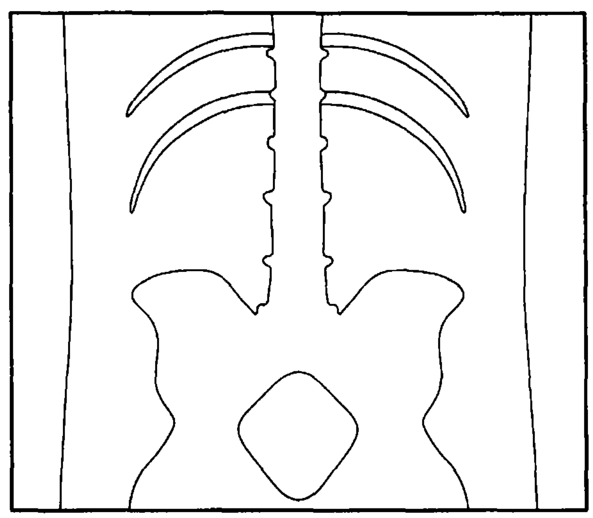
F I G. 8C

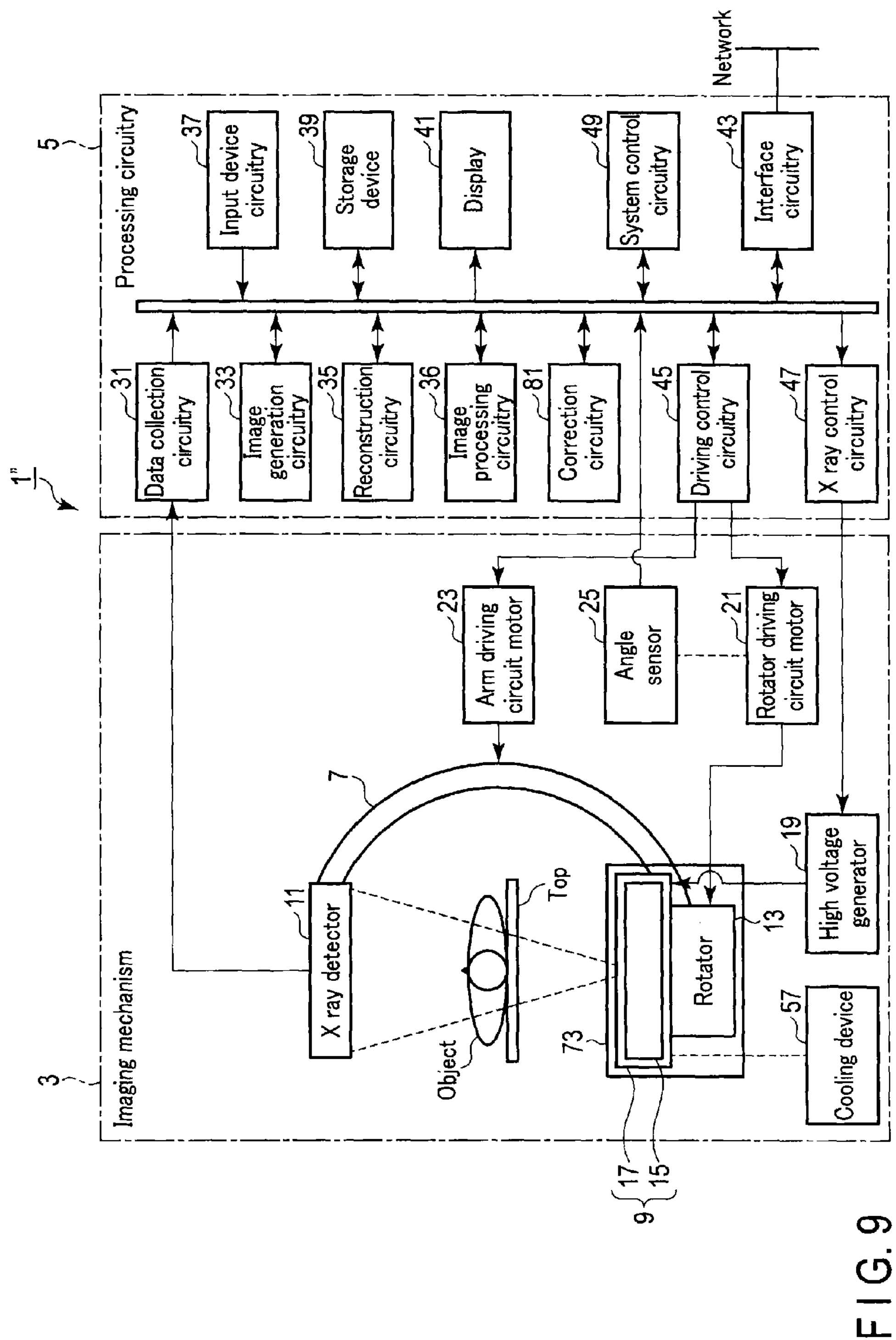
F I G. 9

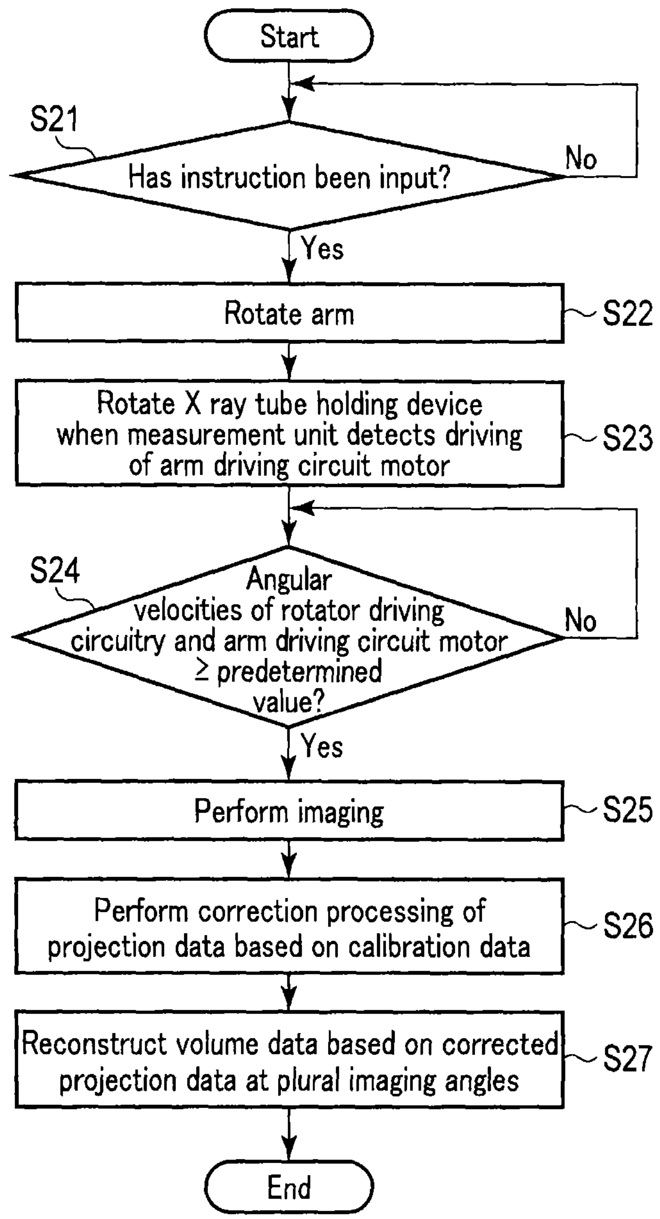
F I G. 10

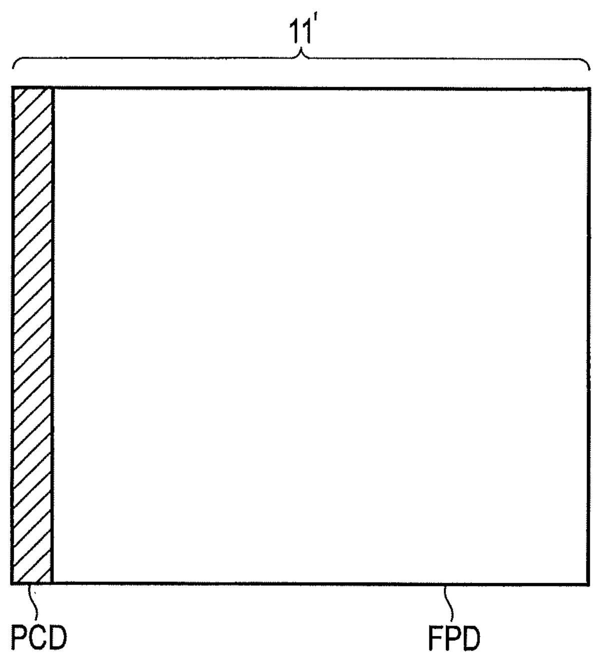
F I G. 12
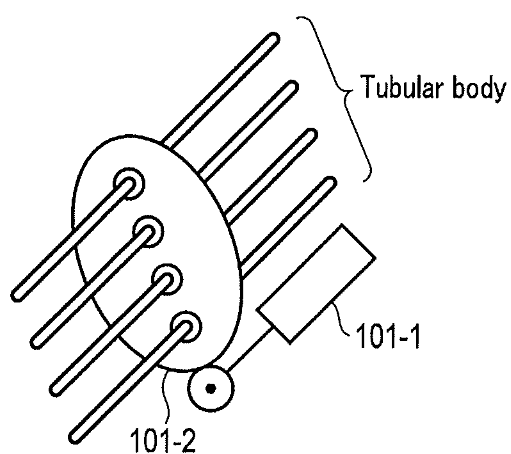
F I G. 13

X-RAY DIAGNOSTIC APPARATUS

CROSS-REFERENCE TO RELATED APPLICATIONS

This application is based upon and claims the benefit of priority from the prior Japanese Patent Application No. 2014-141781, filed Jul. 9, 2014 the entire contents of which are incorporated herein by reference.

FIELD

Embodiments described herein relate generally to an X-ray diagnostic apparatus.

BACKGROUND

Recently, X-ray diagnosis has advanced mainly in the field of circulatory organs with improvements in catheter techniques. For example, an X-ray diagnostic apparatus for diagnosis of circulatory organs is formed from an X-ray generation unit, an X-ray detection unit, a holding device which holds them, a bed, a top, a signal processing unit, a display unit, and the like. The holding device allows X-ray imaging at an optimum position from an optimum direction by causing a C-arm or Ω-arm to pivot, rotate, or move about an object.

CT-like imaging (to be referred to as CTL hereinafter) is performed using an X-ray diagnostic apparatus. CTL is often used since CT imaging can be readily performed during an angiography procedure. More specifically, CTL is a technique of generating a tomographic image like a CT image by reconstructing volume data based on projection data collected while rotating the C-arm. CTL is used for confirmation of blood vessel running in an arteriovenous malformation, determination of plaque characteristics, hepatic arteriography in transcatheter arterial embolization for hepatocellular carcinoma, arterial portography, puncture guidance for, for example, percutaneous radiofrequency ablation as the treatment for malignant tumor in a liver, needle biopsy of each organ such as a lung, kidney, liver, or bone marrow, and the like.

In CTL, however, there is a problem that the C-arm cannot be continuously rotated in one direction, unlike CT. FIG. 14 is a schematic view for explaining torsion of cooling pipes when an arm is rotated according to a conventional example. The cooling pipes include a low-temperature pipe D1 and a high-temperature pipe D2. The low-temperature pipe D1 is a channel for a refrigerant. The high-temperature pipe D2 is a channel for the refrigerant warmed by an X-ray tube. In addition, a cooling device is a power source for circulating the refrigerant within an X-ray tube holding device through the cooling pipes. The cooling device is included in, for example, a column supporting the arm. When the arm is rotated by 360°, the high-temperature pipe D2 is twisted and entangled around the low-temperature pipe D1 by 360°, as shown in FIG. 15. That is, when the arm is continuously rotated in one direction, the low-temperature pipe D1 and the high-temperature pipe D2 are twisted and entangled around each other many times, and eventually break.

The cooling device is not mounted on the C-arm, thereby causing torsion of the cooling pipes. Similarly, a high-voltage generation device for applying a voltage to the X-ray tube is not mounted on the C-arm, thereby causing torsion of a high-voltage line for transferring a high voltage. Since the cooling device and the high-voltage generation device are large in size and heavy, if they are mounted on the C-arm, the C-arm unwantedly becomes large in size. In consideration of arrangement of another medical device near a blood vessel imaging device or an operator who stands near by the blood vessel imaging device to perform a procedure, the C-arm needs to be small in size. Therefore, it is difficult to mount the cooling device and the high-voltage generation device on the C-arm.

BRIEF DESCRIPTION OF THE DRAWINGS

FIG. 3 is a view for explaining the cable systems of an X-ray tube holding device shown in FIG. 1;

FIG. 4 is a view for explaining a principle of reversing torsion of cooling pipes according to the embodiment;

FIG. 6 is a view showing the arrangement of an X-ray diagnostic apparatus according to Application Example 1;

FIG. 8B is a schematic view showing calibration data according to Application Example 2;

FIG. 8C is a schematic view showing an X-ray image obtained by correcting the heel effect by a correction circuitry shown in FIG. 9;

FIG. 9 is a view showing the arrangement of an X-ray diagnostic apparatus according to Application Example 2;

FIG. 10 is a flowchart illustrating the typical procedure of CTL imaging according to Application Example 2;

FIG. 12 is a schematic view showing an X-ray detector according to Application Example 4;

FIG. 13 is a schematic view showing a torsional relaxation mechanism according to Application Example 5;

DETAILED DESCRIPTION

Figure 1:
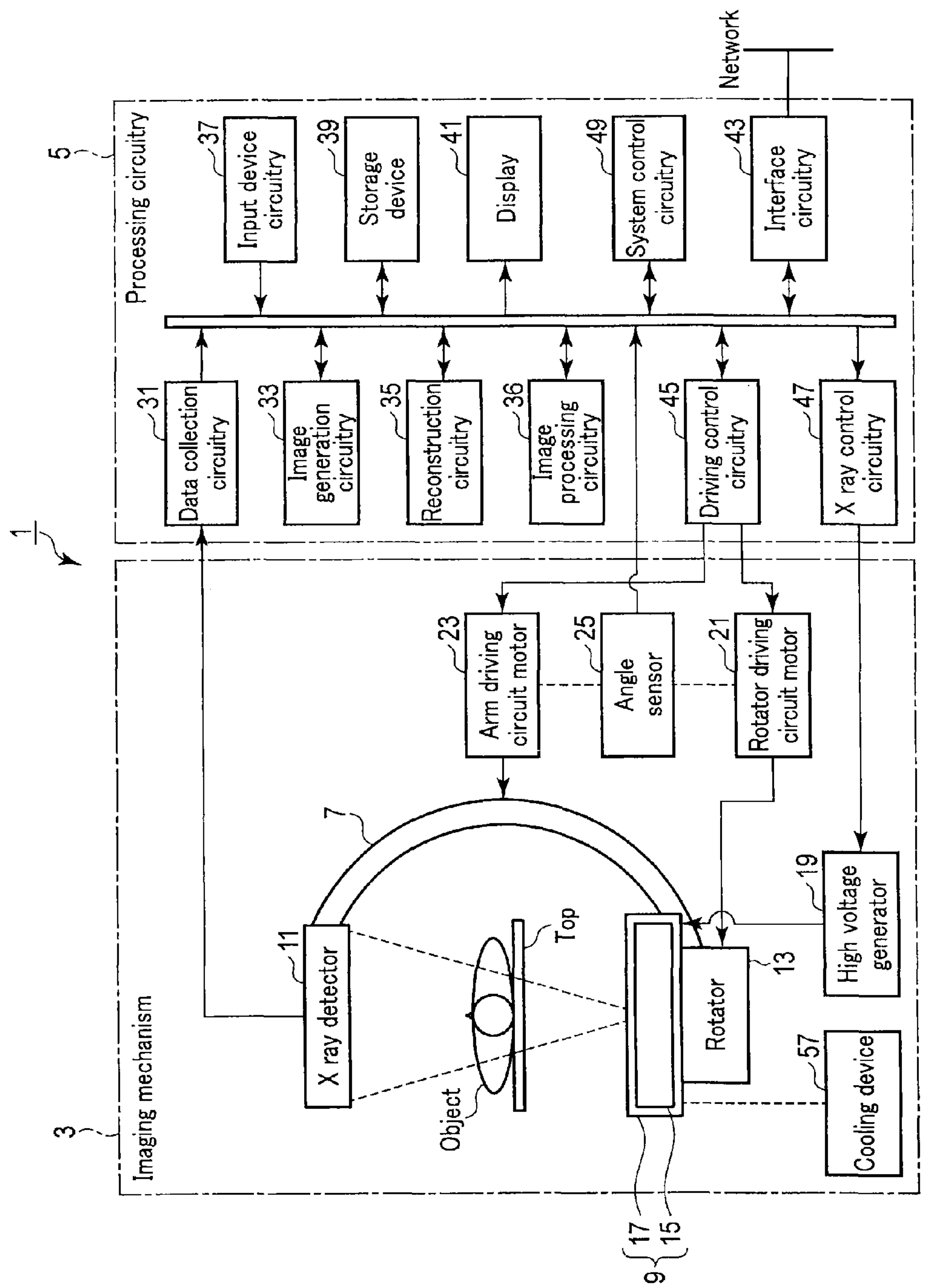
FIG. 1 is a view showing the arrangement of an X-ray diagnostic apparatus according to an embodiment.

An X-ray diagnostic apparatus according to an embodiment includes an X-ray tube holding device configured to generate X-rays, an X-ray detector configured to detect the X-rays, a rotator configured to hold the housing so as to be rotatable about a first rotation axis obtained by setting an irradiation direction of the X-rays as an axis, an arm configured to hold the rotator and the X-ray detector and be rotatable about a second rotation axis different from the first rotation axis, and a tubular body configured to connect the X-ray tube holding device and a device away from the arm, and the arm holds the rotator so as to be rotatable about the first rotation axis in a direction in which torsion of the tubular body is reduced.

A medical image diagnostic apparatus according to the embodiment will be described below with reference to the accompanying drawings. Note that in the following description, the same reference numerals denote components having almost the same functions and arrangements, and a repetitive description thereof will be made, only as needed.

FIG. 1 is a view showing the arrangement of an X-ray diagnostic apparatus 1 according to this embodiment. The X-ray diagnostic apparatus 1 includes an imaging mechanism 3 and a processing circuitry 5.

The imaging mechanism 3 includes an arm 7. The arm 7 supports an X-ray tube holding device 9 and an X-ray detector 11 so as to face each other. More specifically, a rotator 13 is provided on one end of the arm 7. The rotator 13 is a structure for holding the X-ray tube holding device 9 provided on the rotator 13 so as to be rotatable about the first rotation axis (to be referred to as a rotator rotation axis hereinafter). For example, a line connecting the tube focus of an X-ray tube 15 and the center of the detection surface of the X-ray detector 11 is defined as the rotator rotation axis. In this embodiment, the rotator 13 holds the X-ray tube holding device 9 so as to be rotatable about the rotator rotation axis. The X-ray tube holding device 9 includes the X-ray tube 15, and a housing 17 storing the X-ray tube 15. The X-ray tube 15 generates X-rays upon receiving the application of a high voltage from a high-voltage generator 19 and the supply of a filament current. A cooling device 57 supplies, to the X-ray tube holding device 9, a refrigerant to cool the X-ray tube holding device 9. The cooling device 57 also cools the refrigerant heated by the X-ray tube holding device 9. The cooling device 57 is provided outside the arm 7.

The X-ray detector 11 is provided on the other end of the arm 7. The X-ray detector 11 is implemented by, for example, a flat panel detector (FPD). The FPD includes a plurality of pixels arranged two-dimensionally. Each pixel detects the X-rays generated by the X-ray tube 15, and converts the detected X-rays into an electrical signal. The X-ray detector 11 outputs the converted electrical signal to a data collection circuitry 31 (to be described later).

A rotator driving motor 21 generates power to rotate the rotator 13 under the control of a driving control circuitry 45 (to be described later). The rotator driving motor 21 is implemented by, for example, a combination of a memory and a predetermined processor for executing a program. The rotator 13 rotates by receiving the power from the rotator driving motor 21. An arm driving motor 23 generates power to rotate the arm 7 under the control of the driving control circuitry 45 (to be described later). The arm driving motor 23 is implemented by, for example, a combination of a memory and a predetermined processor for executing a program. The arm 7 rotates by receiving the power from the arm driving motor 23. The rotator driving motor 21 and the arm driving motor 23 are, for example, motors or servomotors.

An angle sensor 25 measures the angle of the rotator 13. The angle sensor 25 measures the angle of the arm 7. More specifically, the angle sensor 25 is implemented by, for example, a rotary encoder. The driving control circuitry 45 measures the angular velocity of the rotator 13 based on an angle signal from the rotary encoder 25. The driving control circuitry 45 measures the angular velocity of the arm 7 based on an angle signal from the rotary encoder 25. The rotary encoder 25 is attached to the rotation shaft of each of the rotator driving motor 21 and arm driving motor 23. The rotary encoder 25 outputs a rotational displacement of each of the rotator driving motor 21 and arm driving motor 23 as a digital signal. The angle sensor 25 measures an imaging angle, and outputs it to an imaging control circuitry 29.

The processing circuitry 5 includes the data collection circuitry 31, an image generation circuitry 33, a reconstruction circuitry 35, an image processing circuitry 36, an input circuitry 37, a storage 39, a display 41, an interface circuitry 43, the driving control circuitry 45, an X-ray control circuitry 47, and a system control circuitry 49. The processing circuitry 5 is implemented by, for example, a combination of a memory and a predetermined processor for executing a program.

The data collection circuitry 31 reads out the electrical signal of each pixel of the X-ray detector 11, and digitally converts the readout electrical signal to generate digital data. The data collection circuitry 31 is implemented by, for example, a combination of a memory and a predetermined processor for executing a program. More specifically, the data collection circuitry 31 includes an I-V converter for converting the electrical signal of each pixel of the X-ray detector 11 into a voltage, an integrator for periodically integrating the voltage signal in synchronism with an irradiation period of X-rays, an amplifier for amplifying an output signal from the integrator, and an analog-to-digital converter for converting an output signal from the amplifier into a digital signal. The data collection circuitry 31 outputs the digital data to the image generation circuitry 33.

The image generation circuitry 33 performs preprocessing such as log conversion for the digital data output from the data collection circuitry 31, thereby generating projection data. More specifically, the image generation circuitry 33 continuously generates fluoroscopic images based on a plurality of continuous X-ray data which have been detected by the X-ray detector 11 while the arm 7 rotates about the arm rotation axis. The image generation circuitry 33 is implemented by, for example, a combination of a memory and a predetermined processor for executing a program. Note that the image generation circuitry 33 may generate an X-ray image based on the digital data output from the X-ray detector 11. The image generation circuitry 33 outputs the generated projection data and X-ray image to the storage 39. The projection data is stored in the storage 39 in association with the imaging angle. The imaging angle indicates the rotation angle of the arm 7 about the second rotation axis (to be referred to as an arm rotation axis hereinafter). The second rotation axis is an axis which passes through a holding mechanism and intersects the rotator rotation axis when the arm 7 is at the initial position. The reconstruction circuitry 35 reconstructs volume data based on projection data about a plurality of imaging angles stored in the storage 39. The reconstruction circuitry 35 is implemented by, for example, a combination of a memory and a predetermined processor for executing a program. The reconstructed volume data is stored in the storage 39. The image processing circuitry 36 performs various image processes for the volume data. The image processing circuitry 36 is implemented by, for example, a combination of a memory and a predetermined processor for executing a program. For example, the image processing circuitry 36 performs three-dimensional image processing for the volume data to generate a two-dimensional display image. In the three-dimensional image processing, for example, volume rendering, surface rendering, MPR (Multi-Planar Reformat) rendering, pixel value projection processing, and the like are performed for the volume data. The image processing circuit 36 performs perfusion analysis for the volume data.

The input circuitry 37 inputs various instructions, commands, pieces of information, selections, settings, and the like from an operator or the like to the system control circuitry 49.

The storage 39 stores an operator instruction supplied from the input circuitry 37. The storage 39 stores various kinds of data. The storage 39 may also store the projection data, the X-ray image, and the like which have been generated by the image generation circuitry 33. The storage 39 outputs the stored projection data and X-ray image to the reconstruction circuitry 35, display 41, interface circuitry 43, and the like, as needed.

The display 41 displays various kinds of information on a monitor. The display 41 displays, for example, the X-ray image generated by the image generation circuitry 33. The display 41 displays, for example, a tomographic image generated based on the volume data reconstructed by the reconstruction circuitry 35. The display 41 may load and display an arbitrary image stored in the storage 39.

The interface circuitry 43 is connected to a PACS (Picture Archiving and Communication Systems) and other computers (none are shown) via a network.

The driving control circuitry 45 periodically controls the rotator driving motor 21 and arm driving motor 23 so as to rotate the rotator 13 about the rotator axis in accordance with rotation of the arm 7 about the arm rotation axis. The driving control circuitry 45 is implemented by, for example, a combination of a memory and a predetermined processor for executing a program. The X-ray control circuitry 47 controls the high-voltage generator 19 in accordance with an instruction from the system control circuitry 49. The X-ray control circuitry 47 is implemented by, for example, a combination of a memory and a predetermined processor for executing a program. More specifically, when CTL is performed, if the angular velocity of each of the rotator driving motor 21 and arm driving motor 23, which has been measured by the angle sensor 25, is equal to or higher than a predetermined value, the X-ray control circuitry 47 causes the high-voltage generator 19 to apply a high voltage to the X-ray tube 15 and supply a filament current to the X-ray tube 15. Upon receiving the application of the high voltage and the supply of the filament current, the X-ray tube 15 generates X-rays.

The system control circuitry 49 serves as the main unit of the X-ray diagnostic apparatus 1. The system control circuitry 49 is implemented by, for example, a combination of a memory and a predetermined processor for executing a program. The system control circuitry 49 comprehensively controls the respective components of the X-ray diagnostic apparatus 1, thereby implementing various operations according to this embodiment.

Figure 2:
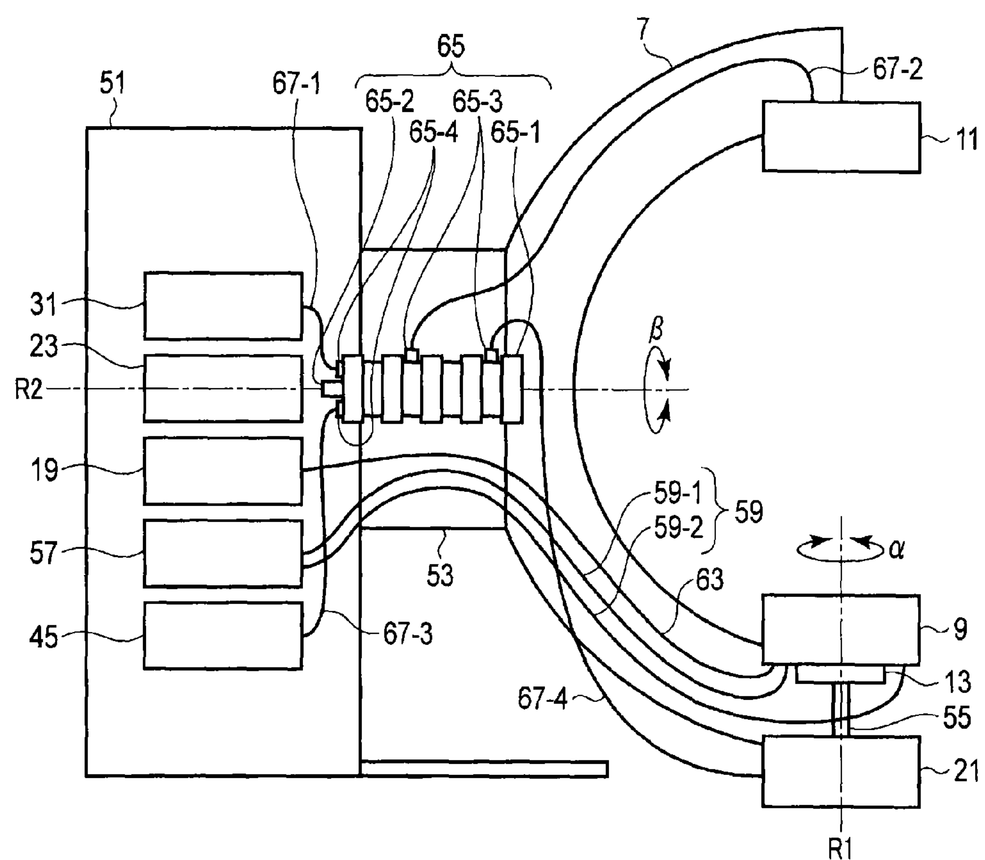
FIG. 2 is a schematic view showing a side surface of an imaging mechanism according to the embodiment.

FIG. 2 is a schematic view showing a side surface of the imaging mechanism 3 according to this embodiment. The rotation mechanism and cable systems of the imaging mechanism 3 according to this embodiment will be described with reference to FIG. 2. Each cable system is a tubular body for connecting the X-ray tube holding device 9 and a device away from the arm 7. Each cable system will be referred to as a tubular body hereinafter. The device away from the arm 7 is, specifically, the high-voltage generator 19 or cooling device 57. That is, if the device is the high-voltage generator 19, the tubular body is a high-voltage line for supplying a high voltage generated by the high-voltage generator 19 to the X-ray tube holding device 9. If the device is the cooling device 57, the tubular body is a refrigerant pipe for circulating a refrigerant between the cooling device 57 and the X-ray tube holding device 9.

The rotation mechanism of the imaging mechanism 3 will be explained first. As shown in FIG. 2, the imaging mechanism 3 includes a column 51, an arm shaft portion 53, and the arm 7. The column 51 is placed on the floor, and supports the arm shaft portion 53 and the arm 7. The column 51 horizontally supports the arm shaft portion 53 apart from the floor. The arm shaft portion 53 mounts a slip ring 65 (to be described later). The arm shaft portion 53 supports the arm 7 so as to be rotatable about a shaft center which is set as an arm rotation axis R2. The rotation direction about the arm rotation axis R2 is represented by a β direction. The arm 7 rotates in the β direction about the arm rotation axis R2 in the β direction by power generated by the arm driving motor 23. Rotation of the arm 7 about the arm rotation axis R2 in the β direction will be referred to as propeller rotation hereinafter.

The X-ray tube holding device 9 is provided on the rotator 13 attached to the arm 7. The X-ray tube holding device 9 is supported by the arm 7 so as to rotate about the shaft center of a rotator shaft portion 55, which is set as a rotator rotation axis R1. The rotation direction about the rotator rotation axis R1 is represented by an a direction. The X-ray tube holding device 9 rotates about the rotator rotation axis R1 in the α direction by power generated by the rotator driving motor 21.

The tubular body of the imaging mechanism 3 will be described next. The cooling device 57 is a power source for circulating the refrigerant within the X-ray tube holding device 9 to cool the X-ray tube 15. The cooling device 57 cools the X-ray tube 15 to cool the returned warm refrigerant. The cooling device 57 is implemented by a motor pump, a cooling circuit for the refrigerant, and the like. The refrigerant may be, for example, an oil or coolant. The cooling device 57 is connected to the X-ray tube holding device 9 via cooling pipes 59. The cooling pipes 59 are pipes for circulating the refrigerant. To provide a detailed description, assume that the cooling device 57 is installed inside the column 51. Note that the cooling device 57 may be installed outside the column 51. The cooling pipes 59 may be arranged inside or outside the arm 7.

Details of the cable systems of the imaging mechanism 3 will be described with reference to FIG. 3. FIG. 3 is a view for explaining the cable systems of the X-ray tube holding device 9 shown in FIG. 1. The cooling pipes 59 include a low-temperature pipe 59-1 and a high-temperature pipe 59-2. The refrigerant circulates between the cooling device 57 and the X-ray tube holding device 9 via the low-temperature pipe 59-1 and the high-temperature pipe 59-2. More specifically, the refrigerant is transferred from the cooling device 57 to the low-temperature pipe 59-1, cools the X-ray tube 15 while circulating in the X-ray tube holding device 9 according to the arrow of a refrigerant flow FL shown in FIG. 3, and returns to the cooling device 57 through the high-temperature pipe 59-2 to be cooled. The X-ray tube holding device 9 includes the X-ray tube 15 and the housing 17. The housing 17 includes cooling pipe connectors 61 for connecting the cooling pipes 59. The cooling pipe connectors 61 include a low-temperature pipe connector 61-1 for connecting the low-temperature pipe 59-1 and a high-temperature pipe connector 61-2 for connecting the high-temperature pipe 59-2. The cooling pipe connectors 61 fix the cooling pipes 59 to prevent the refrigerant from leaking. The housing 17 includes a high-voltage line connector 64 for connecting a high-voltage line 63. Note that a driving unit case 22 is provided to surround the rotator driving motor 21 in order to prevent the cable systems from being entangled around the rotator driving motor 21. Referring back to FIG. 2, the cable systems of the imaging mechanism 3 according to this embodiment will be continuously described. The high-voltage line 63 connects the high-voltage generator 19 and the X-ray tube 15. A high voltage from the high-voltage generator 19 to the X-ray tube 15 is supplied via the high-voltage line 63. The high-voltage line 63 is provided, for example, in the column 51, and runs inside the arm shaft portion 53 and inside or outside the arm 7 to be connected to the X-ray tube 15.

The slip ring 65 is provided across the column 51 and the arm 7. The slip ring 65 is a rotation connector capable of transferring power and an electrical signal from a still object to a rotator. The slip ring 65 includes an annular electrode 65-1, a shaft 65-2, brushes 65-3, and terminals 65-4. The annular electrode 65-1 is provided in the arm shaft portion 53 along the shaft 65-2. The annular electrode 65-1 includes contact portions with the plurality of brushes 65-3 to transfer a plurality of powers and a plurality of electrical signals. The contact portions with the plurality of brushes 65-3 are insulated from each other. The brushes 65-3 are provided in the arm shaft portion 53 for respective transmission lines to rub and contact the annular electrode 65-1. The brushes 65-3 contain elements such as carbon and a wire. The terminals 65-4 electrically connected to the respective contact portions with the plurality of brushes 65-3 are provided on the end of the annular electrode 65-1 on the column side, and connected to transmission lines 67 connected to the respective portions accommodated in the column 51. The transmission lines 67 connected to the X-ray detector 11 and X-ray tube holding device 9 which are accommodated in the arm 7 are also connected to the brushes 65-3. The driving control circuitry 45 and terminal 65-4 are connected by a transmission line 67-3. The brush 65-3 and the X-ray tube holding device 9 are connected by a transmission line 67-2. The data collection circuitry 31 and the terminal 65-4 are connected by a transmission line 67-1. The brush 65-3 and the X-ray detector 11 are connected by a transmission line 67-2.

An electrical signal from the X-ray detector 11 is supplied to the data collection circuitry 31 via the slip ring 65. A driving signal from the driving control circuitry 45 is supplied to the rotator driving motor 21 via the slip ring 65. Note that the electrical signal from the X-ray detector 11 may be supplied to the data collection circuitry 31 by non-contact optical communication. The driving signal from the driving control circuitry 45 may be supplied to the data collection circuitry 31 by non-contact optical communication. Angular velocity information from the rotary encoder attached to the rotation shaft of the rotator driving motor 21 is supplied to the driving control circuitry 45 via the slip ring 65. Note that high-voltage insulation by an insulator or the like is required to transfer high-voltage power but it is difficult for the slip ring 65 to incorporate, in its structure, a high-voltage insulating material such as an insulator to the necessary extent due to a size limitation. In addition, since the slip ring 65 rotates, the insulating material portion is susceptible to damage. Therefore, in this embodiment, the high-voltage line 63 is provided separately from the slip ring 65.

Note that instead of the slip ring 65, non-contact communication and a small storage battery may be used to transfer power and an electrical signal from the device (still object) in the column 51 to the device in the arm 7 (rotator). For non-contact communication, a non-contact communication terminal capable of transmitting/receiving a signal is provided in each of the arm 7 and the column 51. The small storage battery is mounted on the arm 7 to supply power to the rotator driving motor 21, the X-ray detector 11, and the non-contact communication terminal provided in the arm 7. With this arrangement, it is possible to supply the driving signal from the driving control circuitry 45 to the rotator driving motor 21 and the electrical signal from the X-ray detector 11 to the data collection circuitry 31 without the slip ring 65 but there is a problem that the arm 7 becomes large in size and heavy. In consideration of arrangement of another medical device near a blood vessel imaging device or the operator who stands near by the blood vessel imaging device to perform a procedure, the arm needs to be small in size. Consequently, in this embodiment, the slip ring 65 is used instead of non-contact communication and the small storage battery.

Figure 14:
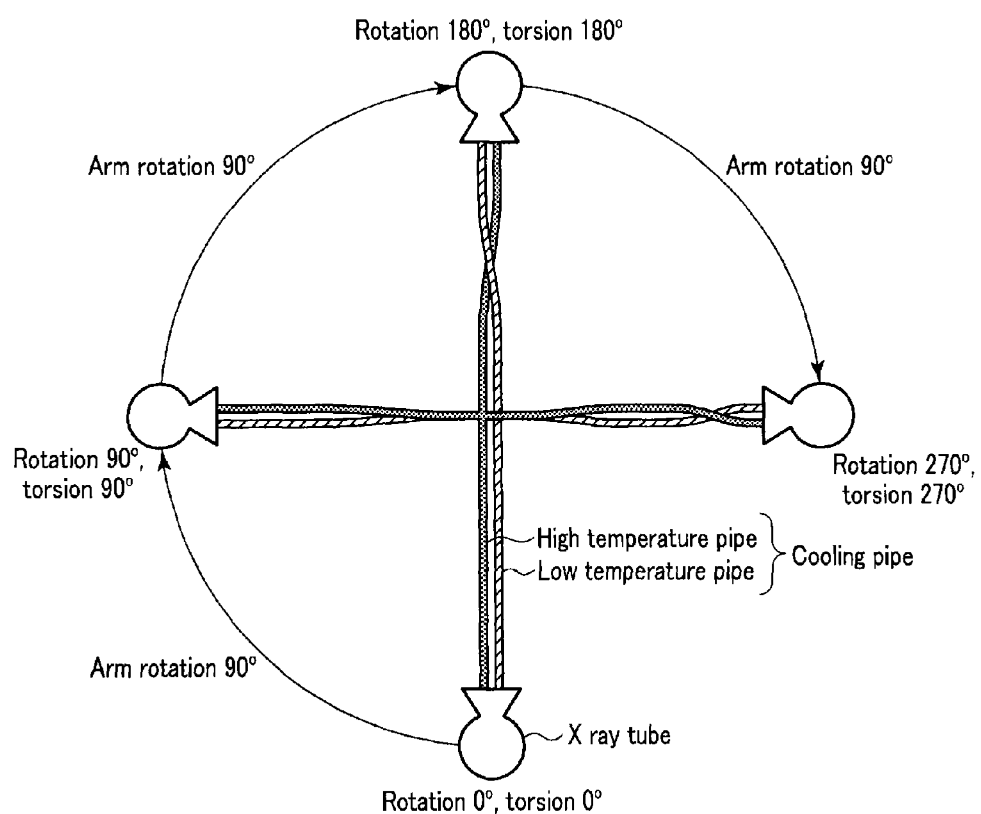
FIG. 14 is a view for explaining torsion of cooling pipes when an arm is rotated according to a conventional example.
Figure 15:
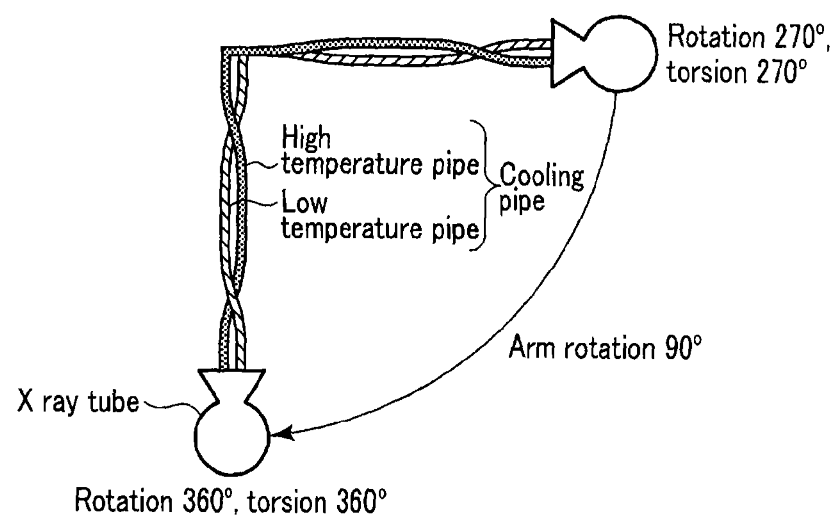
FIG. 15 is a view for explaining torsion of the cooling pipes when the arm is rotated by 360° according to the conventional example.

The rotation mechanism and cable systems of the imaging mechanism 3 according to this embodiment have been described with reference to FIGS. 2 and 3. Torsion of the cable systems along with rotation of the imaging mechanism 3 will be explained with reference to FIGS. 14 and 15. FIG. 14 is a schematic view for explaining torsion of the cooling pipes 59 when the arm is rotated according to the conventional example. FIG. 15 is a schematic view for explaining torsion of the cooling pipes 59 when the arm is rotated by 360° according to the conventional example.

FIG. 14 shows an operation according to the conventional example, in which when the arm is rotated by 90°, 180°, or 270°, the high-temperature pipe 59-2 is twisted and entangled around the low-temperature pipe 59-1 by 90°, 180°, or 270°. FIG. 15 shows an operation according to the conventional example, in which when the arm is rotated by 360°, the high-temperature pipe 59-2 is twisted and entangled around the low-temperature pipe 59-1 by 360°. That is, when the arm 7 is continuously rotated in one direction, the low-temperature pipe 59-1 and the high-temperature pipe 59-2 are twisted and entangled around each other by 360° for each revolution, and eventually break.

Consider a method of reversing torsion between the low-temperature pipe 59-1 and the high-temperature pipe 59-2 by rotating the X-ray tube holding device 9 using the rotator 13 in synchronism with the rotation of the arm 7. FIG. 4 is a view for explaining a principle of reversing torsion of the cooling pipes 59 according to this embodiment. To reverse torsion of the high-temperature pipe 59-2 around the arm rotation axis by 90° in a forward direction with respect to the low-temperature pipe 59-1, the rotator 13 is rotated about the rotator rotation axis by 90° in the forward direction. To reverse torsion of the high-temperature pipe 59-2 about the arm rotation axis by 180° in the forward direction with respect to the low-temperature pipe 59-1, the rotator 13 is rotated about the rotator rotation axis by 180° in the forward direction. That is, the driving control circuitry 45 need only control the rotator driving motor 21 and arm driving motor 23 to equalize the angle of the arm 7 about the arm rotation axis and that of the rotator 13 about the rotator rotation axis. In other words, the driving control circuitry 45 need only control the rotator driving motor 21 and arm driving motor 23 to rotate the arm 7 about the arm rotation axis and the rotator 13 about the rotator rotation axis in the same direction at the same angular velocity. The above control processing by the driving control circuitry 45 can control torsion, thereby making it possible to continuously rotate the arm 7 in one direction.

Note that there is provided a rotary joint as one of means for suppressing torsion of a tubular mechanism. The rotary joint is used by connecting, to another pipe via itself, one pipe connected to a power pump. With power of the power pump, a fluid medium flows inside the pipe connected to the power pump, inside the rotary joint, and inside the pipe connected to the rotary joint. When the rotary joint rotates around the circumference of the pipe, the pile connected to the power pump does not rotate, and only the rotary joint and the pipe connected to it rotate. However, there is a problem with the rotation mechanism of the rotary joint that the medium flowing inside the rotary joint readily leaks. To implement the rotation mechanism, the rotary joint includes a consumable part such as a packing material. In this embodiment, it is very dangerous that the refrigerant such as an oil or coolant leaks. Each cable system according to this embodiment includes no consumable part to rotate the cable system itself in its circumferential direction.

Figure 5:
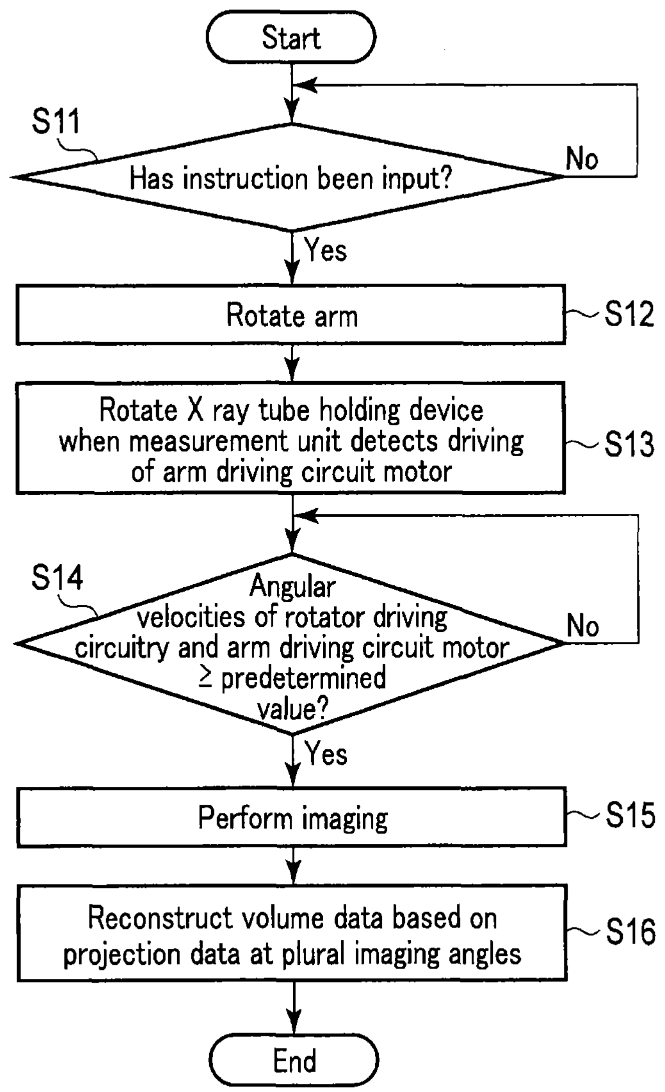
FIG. 5 is a flowchart illustrating the typical procedure of CTL imaging according to the embodiment.

An example of a series of operations according to this embodiment will be described below with reference to FIG. 5. FIG. 5 is a flowchart illustrating the typical procedure of CTL imaging according to this embodiment. Assume that an object has been placed on the top for imaging in advance, and alignment between the top and the arm 7 is complete.

The system control circuitry 49 stands by for the input of an imaging start instruction via the input circuitry 37 by the operator (step S11). If the system control circuitry 49 determines in step S11 that an imaging start instruction has been input, the process advances to step S12.

If it is determined in step S11 that an imaging start instruction has been input, the system control circuitry 49 sends a rotation instruction signal to the driving control circuitry 45 to rotate the arm 7 (step S12). In step S12, the driving control circuitry 45 drives the arm driving motor 23 to rotate the arm 7.

After the processing in step S12 is performed, when the angle sensor 25 detects driving of the arm driving motor 23, the system control circuitry 49 rotates the X-ray tube holding device 9 under the control of the driving control circuitry 45 (step S13). In step S13, the driving control circuitry 45 drives the rotator driving motor 21 to rotate the rotator 13. When the rotator 13 rotates, the X-ray tube holding device 9 held by the rotator 13 rotates with the rotator 13. Torsion of the cooling pipes 59 and the high-voltage line 63 which are connected to the X-ray tube holding device 9 is suppressed by rotating the X-ray tube holding device 9 about the rotator rotation axis in accordance with rotation of the arm 7 about the arm rotation axis.

Note that if the rotation angular velocities of the arm 7 and rotator 13 are suddenly increased, the arm 7 may crash against the object, top, peripheral devices, and operator. The driving control circuitry 45 controls the arm driving motor 23 and rotator driving motor 21 in synchronism with each other, and gradually increases the rotation angular velocities of the arm 7 and rotator 13 toward an irradiation start angular velocity.

After the processing in step S13 is performed, the system control circuitry 49 determines whether the rotation angular velocities of the arm 7 and rotator 13 are equal to or higher than the irradiation start angular velocity (step S14). The irradiation start angular velocity has the value of an angular velocity at the start of X-ray irradiation, and is stored in the storage 39 in advance. If it is determined in step S14 that the rotation angular velocities of the arm 7 and rotator 13 are equal to or higher than the irradiation start angular velocity, the process advances to step S15.

If it is determined in step S14 that the rotation angular velocities of the arm 7 and rotator 13 are equal to or higher than the predetermined value, the system control circuitry 49 controls the driving control circuitry 45 and X-ray control circuitry 47 in synchronism with each other to start imaging (step S15). In step S15, the X-ray control circuitry 47 sends an instruction signal to the high-voltage generator 19 to apply a high voltage to the X-ray tube 15 and supply a filament current to the X-ray tube 15. Upon receiving the application of the high voltage and the supply of the filament current by the high-voltage generator 19, the X-ray tube 15 starts X-ray irradiation. The X-ray detector 11 detects X-rays emitted by the X-ray tube 15. The data collection circuitry 31 collects digital data obtained by digitally converting the electrical signals of the respective pixels of the X-ray detector 11, and outputs the digital data to the image generation circuitry 33. The image generation circuitry 33 performs preprocessing such as log conversion for the digital data output from the data collection circuitry 31, thereby generating projection data. The X-ray diagnostic apparatus 1 according to this embodiment performs imaging by causing the arm 7 to make a plurality of revolutions, thereby generating projection data at each imaging angle for every revolution.

After the processing in step S15 is performed, the system control circuitry 49 causes the reconstruction circuitry 35 to reconstruct volume data based on the projection data at the plurality of imaging angles (step S16). The reconstruction circuitry 35 can reconstruct single volume data based on the projection data for every revolution. Since the projection data are acquired by causing the arm 7 to continuously make a plurality of revolutions, the reconstruction circuitry 35 can reconstruct volume data in time series based on the projection data for the plurality of revolutions. It is possible to acquire volume data in time series at a frame rate corresponding to the rotation angular velocity of the arm 7 by causing the arm 7 to continuously make a plurality of revolutions while keeping the top at the same position, and performing imaging. Four-dimensional CT can be implemented in this embodiment.

The typical procedure of CTL imaging according to this embodiment has been explained above. This embodiment is also used for examination like CT perfusion (to be referred to as CTP hereinafter) or the like. CTP is an examination method of measuring a vascular flow in a brain using CT and a contrast medium. The image processing circuitry 36 performs perfusion analysis for the volume data in time series to calculate an index such as a blood flow rate. Note that this embodiment is also applicable to electrocardiogram scanning.

Note that the above description assumes the C-arm shown in FIG. 2 as an arm. In imaging during an angiography procedure using the C-arm, the operator can ensure a procedure space beside the object by setting the C-arm at a position where the head of the object lying on the top is to put in, and performing CTL imaging by propeller rotation. Therefore, the C-arm is appropriately used as the arm according to this embodiment. For the same reason, that is, in order to ensure the procedure space during imaging, a ceiling suspended Ω-arm may be used, as a matter of course.

On the other hand, as the shape of the arm for implementing CTL imaging, there is an O-arm surrounding a target portion (for example, an abdominal region) of the object by an arm. The O-arm is an arm having an annular shape, and the top is set in the circle. It is possible to perform CTL imaging while the X-ray tube and X-ray detector rotate by 360° inside the O-arm. When performing imaging using the O-arm, however, it is necessary to perform imaging by closing the arm to surround the abdominal region of the object, and it is thus necessary to perform imaging by setting the arm beside the object lying on the top. Therefore, the operator cannot ensure the procedure space beside the object. That is, to perform a procedure after imaging, the operator needs to open the closed O-arm, and move the open O-arm from the vicinity of the object. Consequently, imaging using the O-arm during an angiography procedure requires a lot of time and effort.

As described above, the X-ray diagnostic apparatus 1 according to this embodiment can suppress torsion between the cooling pipes 59 and the high-voltage line 63 along with rotation of the arm 7 by rotating the rotator 13 in accordance with the rotation of the arm 7. That is, the arm 7 can be rotated by 360° or more in one direction, that is, can be continuously rotated. Therefore, continuous rotation scanning like CT can be implemented by CTL during an angiography procedure.

Various application examples of this embodiment will be described next. Note that in the following description, the same reference numerals as those in this embodiment denote components having almost the same functions, and a repetitive description thereof will be made, only as needed.

Application Example 1

FIG. 6 is a view showing the arrangement of an X-ray diagnostic apparatus 1-1 according to Application Example 1. The X-ray diagnostic apparatus 1-1 includes an irradiation field limiter 71 and an X-ray tube case 73 in addition to the X-ray diagnostic apparatus 1 of the aforementioned embodiment. The irradiation field limiter 71 limits the irradiation field of X-rays generated by an X-ray tube 15. The irradiation field limiter 71 is directly provided in an X-ray tube holding device 9. When the X-ray tube holding device 9 is rotated, the irradiation field limiter 71 also rotates, similarly to the X-ray tube holding device 9. The rotation of the irradiation field limiter 71 indicates the rotation of the irradiation field with respect to the detection surface of an X-ray detector 11. The X-ray diagnostic apparatus 1-1 according to Application Example 1 does not rotate the irradiation field limiter 71 about the rotator rotation axis even when the X-ray tube holding device 9 is rotated about the rotator rotation axis.

Figure 7:
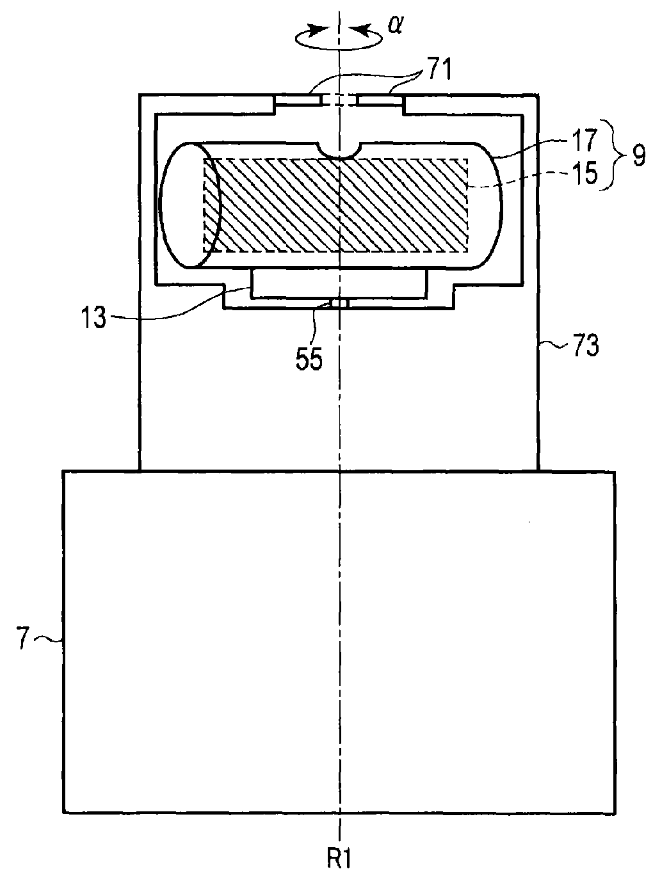
FIG. 7 is a view showing a case in which an irradiation field limiter is installed according to Application Example 1.

FIG. 7 is a view showing an example of installation of the irradiation field limiter 71 according to Application Example 1. The X-ray tube case 73 is connected to the arm 7 to surround the X-ray tube holding device 9. The irradiation field limiter 71 is fixed to the X-ray tube case 73 independently of a rotator 13. The irradiation field limiter 71 and the rotator 13 are fixed independently of each other. The irradiation field limiter 71 is provided in the X-ray tube case 73 so that the rotation of the rotator 13 does not rotate the irradiation field limiter 71.

As described above, even when the X-ray tube holding device 9 is rotated about the rotator rotation axis, the irradiation field limiter 71 does not rotate about the rotator rotation axis, and thus the irradiation field does not rotate with respect to the detection surface of the X-ray detector 11. That is, the irradiation field on the detection surface of the X-ray detector 11 can be made to have the same shape at any imaging angle.

Application Example 2

The radiation intensity distribution of X-rays emitted by an X-ray tube is biased on the anode and cathode sides of the X-ray tube due to the heel effect. Therefore, in the aforementioned embodiment, when the X-ray tube 15 is rotated about the rotator rotation axis, the acquired projection data is influenced by the heel effect which is different depending on the imaging angle. That is, each of projection data imaged at different imaging angles or projection data imaged at different rotation angles of the X-ray tube 15 about the rotator rotation axis includes noise caused by the heel effect according to the rotation angle.

Figure 8A:
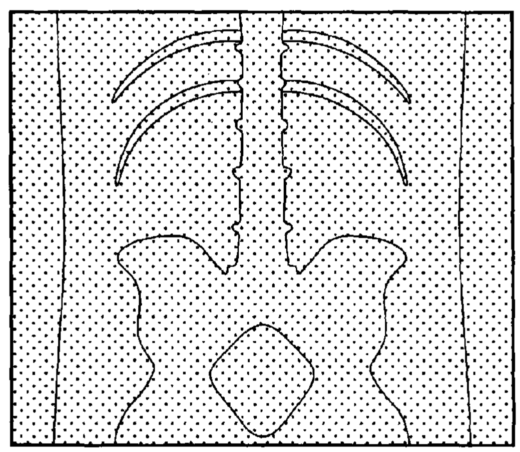
FIG. 8A is a schematic view showing an X-ray image influenced by the heel effect according to Application Example 2.

FIG. 8A is a schematic view showing an X-ray image influenced by the heel effect according to Application Example 2. For the sake of descriptive convenience, instead of projection data, an X-ray image is used to provide a description. An X-ray diagnostic apparatus 1-2 according to Application Example 2 collects projection data while no object is placed on a top before imaging. Projection data or X-ray image generated by imaging (calibration scanning) while no object is placed on the top will be referred to as calibration data hereinafter. FIG. 8B is a schematic view showing the calibration data according to Application Example 2.

FIG. 9 is a view showing the arrangement of the X-ray diagnostic apparatus 1-2 according to Application Example 2. The X-ray diagnostic apparatus 1-2 according to Application Example 2 includes a correction circuit 81 in a processing circuitry 5 in addition to the embodiment of Application Example 1. The correction circuit 81 corrects the projection data or X-ray images at the plurality of imaging angles based on the calibration data. FIG. 8C is a schematic view showing an X-ray image obtained by correcting the heel effect by the correction circuit 81 shown in FIG. 9. The image shown in FIG. 8C is generated by subtracting the image shown in FIG. 8B from that shown in FIG. 8A.

An example of a series of operations according to this embodiment will be described below with reference to FIG. 10. FIG. 10 is a flowchart illustrating the typical procedure of CTL imaging according to Application Example 2. The object is placed on the top in advance for imaging, and alignment between the top and an arm 7 is complete. The calibration data have been generated by calibration imaging. The calibration data have been generated at a plurality of imaging angles in the rotation of the arm 7.

A system control circuitry 49 stands by for the input of an imaging start instruction via an input circuitry 37 by the operator (step S21). If the system control circuitry 49 determines in step S21 that an imaging start instruction has been input, the process advances to step S22. Note that processes in steps S21 to S25 are the same as those in steps S11 to S15 (FIG. 5) in the operation example of the aforementioned embodiment and a detailed description thereof will be omitted.

If it is determined in step S21 that an imaging start instruction has been input, the system control circuitry 49 sends a rotation instruction signal to a driving control circuitry 45 to rotate the arm 7 (step S22).

After the processing in step S22 is performed, when an angle sensor 25 detects driving of an arm driving motor 23, the system control circuitry 49 rotates the X-ray tube holding device 9 under the control of the driving control circuitry 45 (step S23).

After the processing in step S23 is performed, the system control circuitry 49 determines whether the rotation angular velocities of the arm 7 and a rotator 13 are equal to or higher than an irradiation start angular velocity (step S24). If it is determined in step S24 that the rotation angular velocities of the arm 7 and rotator 13 are equal to or higher than the irradiation start angular velocity, the process advances to step S25.

If it is determined in step S24 that the rotation angular velocities of the arm 7 and rotator 13 are equal to or higher than the predetermined value, the system control circuitry 49 controls the driving control circuitry 45 and an X-ray control circuitry 47 in synchronism with each other to start imaging (step S25). In step S25, an image generation circuitry 33 generates projection data.

After the processing in step S25 is performed, the system control circuitry 49 causes the correction circuit 81 to perform the correction processing of the projection data based on the calibration data (step S26). In step S26, the correction circuit 81 generates corrected projection data at the plurality of imaging angles by performing the correction processing for the projection data at the plurality of imaging angles in the rotation of the arm 7 by using the corresponding calibration data.

After the processing in step S26 is performed, the system control circuitry 49 causes the reconstruction circuitry 35 to reconstruct volume data based on the corrected projection data at the plurality of imaging angles (step S27).

As described above, the X-ray diagnostic apparatus 1-2 according to Application Example 2 can reduce noise caused by the heel effect in the projection data and X-ray images captured at different rotation angles of the X-ray tube 15 about the rotator rotation axis by performing image processing based on the calibration data. Therefore, it is possible to acquire projection data with reduced influence of the heel effect according to the imaging angle.

Application Example 3

Figure 11:
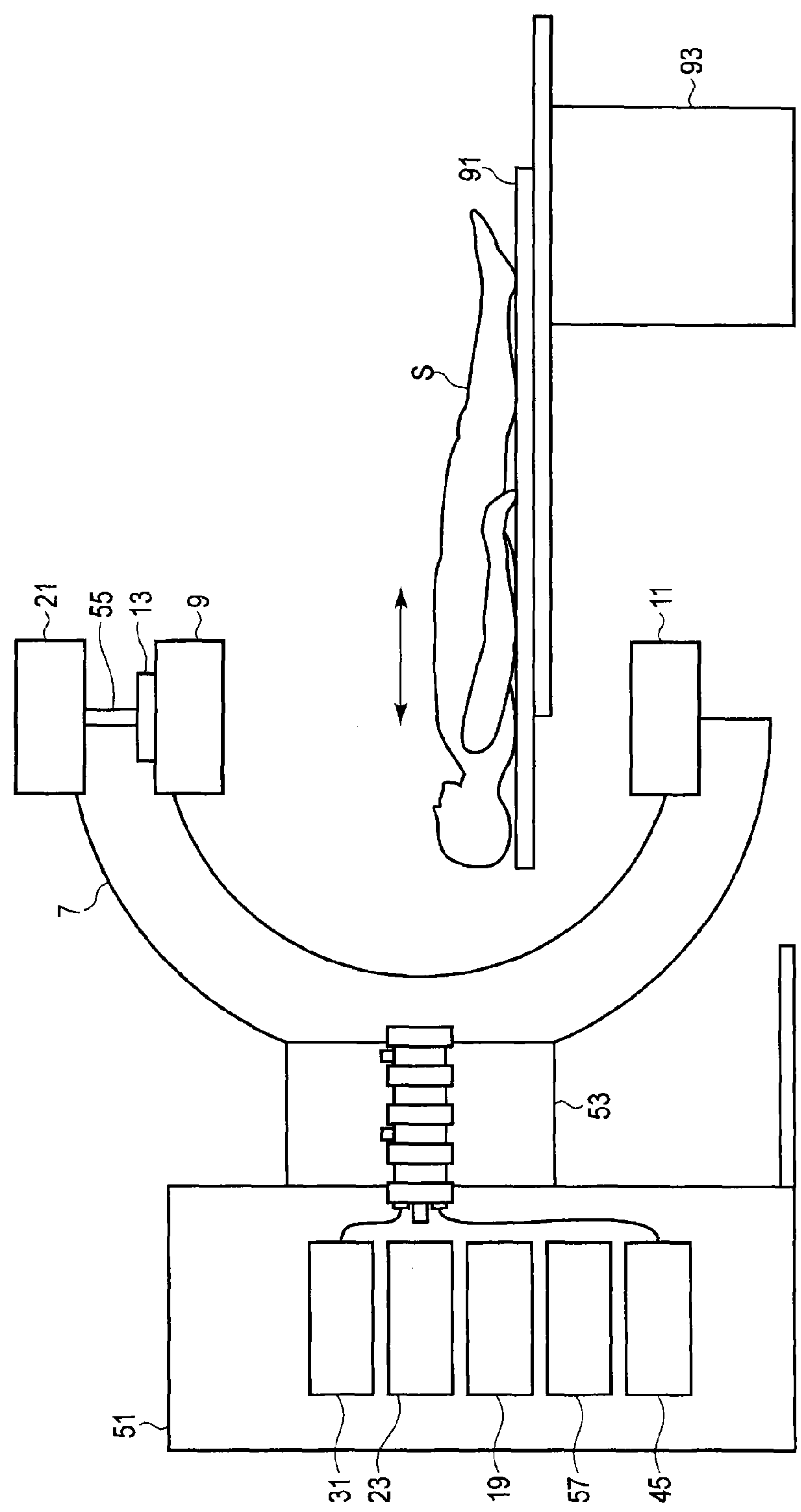
FIG. 11 is a schematic view showing an X-ray diagnostic apparatus according to Application Example 3.

FIG. 11 is a schematic view showing an X-ray diagnostic apparatus 1-3 according to Application Example 3. The X-ray diagnostic apparatus 1-3 includes a top 91 and a bed 93 in addition to the X-ray diagnostic apparatus of the aforementioned embodiment. The top 91 is a plate on which an object S is placed. The top 91 is formed by carbon, fiber reinforced plastic, or the like. The bed 93 supports the top 91 to be slidable in the longitudinal direction. The bed 93 is installed on the floor of an examination room. The bed 93 has a vertically movable mechanism, and can freely adjust the height of the top 91. The bed 93 is formed by a metal, plastic, or the like.

A driving control circuitry 45 moves the top 91 along the body axis direction of the object while the arm 7 continuously rotates by 360° or more about the arm rotation axis. The driving control circuitry 45 can implement helical scanning by performing CTL imaging while sliding the top 91, similarly to CT. More specifically, the driving control circuitry 45 arranges the arm 7 so as not to interfere with sliding of the top 91. For example, the arm is arranged in the head direction of the object, as shown in FIG. 11. Helical scanning by CTL is implemented by performing propeller rotation of the arm 7 to perform CTL imaging while sliding the top 91 in the longitudinal direction. Note that helical scanning can also be implemented by sliding the arm in the same direction instead of the top 91.

As described above, with the X-ray diagnostic apparatus 1-3 according to Application Example 3, it is possible to implement helical scanning by CTL. Therefore, it is possible to continuously collect projection data in a wide range in the craniocaudal direction of the object.

Application Example 4

A photon counting CT (Photon Counting Computed Tomography) (to be referred to as PCCT hereinafter) capable of discriminating the pulse height has been developed as a next-generation CT system. A data collection circuit for general CT converts the current signal of each channel of an X-ray detector into a voltage, periodically integrates the voltage signal in synchronism with an irradiation period of X-rays, and outputs data. Since, however, general CT performs integration, there is a problem that low-energy information is hidden by another energy information.

On the other hand, in PCCT, electric signals generated when the radiation detector detects X-rays are counted in each of a plurality of energy bands, and the counted value is indirectly detected as the number of photons of the X-rays. Since, unlike general CT, X-rays are detected based on data separated for each of the plurality of energy bands, PCCT solves the problem that low-energy information is hidden like general CT.

FIG. 12 is a schematic view showing an X-ray detector 11' according to Application Example 4. The X-ray detector 11' according to Application Example 4 includes a photon counting detector (to be referred to as a PCD hereinafter) near the FPD. Referring to FIG. 12, the PCD is arranged in a linear shape beside the FPD. The PCD may be arranged in the slice direction or channel direction. It is technically impossible to implement the PCD by a detector having an area as wide as FPD. Therefore, the PCD has a rectangular or square shape of several cm×several cm.

An X-ray diagnostic apparatus 1-4 according to Application Example 4 performs X-ray imaging using the X-ray detector 11' in which the FPD and PCD are arranged in a linear shape. In general, an irradiation field is set in the FPD to perform X-ray imaging, similarly to the aforementioned embodiment. At the time of use of the PCD, an irradiation field is set in the PCD to perform X-ray imaging. Note that the FPD and PCD need not be arranged in a linear shape. The PCD may be movably provided near the moving amount of the FPD. More specifically, for example, the PCD may be retracted from the irradiation field of the FPD at the time of normal imaging, and may come out in front of the FPD at the time of PCD imaging. The PCD can move in a direction almost parallel to the detection surface of the FPD in front of the detection surface under the control of the driving control circuitry 45. This allows X-ray imaging by the PCD in which a region of interest has been set.

A data collection circuitry 31 collects count data representing the count of radiation detected by the X-ray detector 11' for the plurality of energy bands. The data collection circuitry 31 is implemented by, for example, a combination of a memory and a predetermined processor for executing a program.

A reconstruction circuitry 35 reconstructs volume data based on the count data.

Furthermore, similarly to Application Example 3, the operator may perform helical scanning by selecting the PCD in the X-ray diagnostic apparatus 1-4.

As described above, the X-ray diagnostic apparatus 1-4 according to Application Example 4 can implement X-ray imaging by using the PCD. Therefore, it is possible to solve the problem that low-energy information is hidden like general CTL.

Application Example 5

If cooling pipes 59 and a high-voltage line 63 (referred to as the tubular bodies in the above description) which are connected to an X-ray tube holding device 9 are long, even if torsional cancellation according to the aforementioned embodiment is performed, it may be impossible to completely cancel the torsion halfway through the tubular bodies in the length direction. In addition, for example, if the tubular bodies are difficult to rotate, even if the X-ray tube holding device 9 rotates, the tubular bodies themselves cannot sufficiently rotate, and thus it may be impossible to completely cancel the torsion. When the friction between a tube collectively holding a plurality of tubular bodies in itself and the tubular bodies held in the tube is strong, it may be impossible to completely cancel the torsion. An X-ray diagnostic apparatus 1-5 according to Application Example 5 includes, between the X-ray tube holding device 9 and a device (a cooling device or high-voltage generator), a torsional relaxation mechanism 99 for relaxing torsion caused by rotations of the tubular bodies by performing rotation in synchronism with rotation of the X-ray tube holding device 9.

The torsional relaxation mechanism 99 is installed between the X-ray tube holding device 9 and the device such as a cooling device or high-voltage generation device. The torsional relaxation mechanism 99 relaxes torsion caused by rotations of the tubular bodies by performing rotation in synchronism with rotation of the X-ray tube holding device 9. FIG. 13 is a schematic view showing the torsional relaxation mechanism 99 according to Application Example 5. The torsional relaxation mechanism 99 includes a motor 99-1 and a disk 99-2 with holes. The motor 99-1 and the disk 99-2 with the holes mesh with, for example, a gear and belt, and the disk 99-2 with the holes rotates in accordance with rotation of the motor 99-1. The torsional relaxation mechanism 99 is provided in the tube. A plurality of tubular bodies running inside the tube penetrate the disk 99-2. When the motor 99-1 rotates the disk 99-2 in synchronism with rotation of the X-ray tube holding device 9, the plurality of tubular bodies rotate similarly to the disk 99-2, thereby relaxing the torsion of the tubular bodies. More specifically, the torsional relaxation mechanism 99 calculates a ratio by dividing the length of the tube from the rotation center of the arm 7 to the torsional relaxation mechanism 99 by the length of the tube from the rotation center of the arm 7 to the X-ray tube holding device 9. Torsion is canceled by rotating the disk according to the calculated ratio.

Note that the ratio may be obtained by another equation.

As described above, the X-ray diagnostic apparatus 1-5 according to Application Example 5 can rotate the arm 7 in one direction by 360° or more, that is, can continuously rotate the arm 7 even when the cables are difficult to rotate or the friction between the tube and the cables held in the tube is strong. Therefore, continuous rotation scanning like CT can be implemented by CTL during an angiography procedure.

Application Example 6

The rotator according to the aforementioned embodiment is rotated by the rotator driving motor 21 in accordance with rotation of the arm. However, the embodiment is not limited to this. It is not necessary to provide the control circuit, rotator driving circuit, and driving control circuit as long as the rotator can rotate by the mechanical effect transferred via the tubular bodies in synchronism with rotation of the arm.

According to this embodiment, it is possible to provide an X-ray diagnostic apparatus capable of improving the procedure efficiency.

Note that the word "processor" in the above description means, for example, a dedicated or general-purpose processor, circuit (circuitry), processing circuit (circuitry), operation circuit (circuitry), arithmetic circuit (circuitry), an ASIC (Application Specific Integrated Circuit), or a programmable logic device (for example, an SPLD (Simple Programmable Logic Device), CPLD (Complex Programmable Logic Device), or FPGA (Field Programmable Gate Array)). In addition, each constituent element (each processing unit) of this embodiment may be implemented by a plurality of processors as well as a single processor. Furthermore, a plurality of constituent elements (a plurality of processing units) may be implemented by a single processor.

Some embodiments of the present invention have been described above. However, these embodiments are presented merely as examples and are not intended to limit the scope of the invention. These novel embodiments can be carried out in various other forms, and various omissions, replacements, and changes can be made without departing from the spirit of the invention. The embodiments and their modifications are also incorporated in the scope and the spirit of the invention as well as in the invention described in the claims and their equivalents.

In addition, each function according to each embodiment can be implemented by installing a scattered radiation correction processing program in a computer such as a workstation and loading it into the memory. In this case, the program which can cause the computer to execute the corresponding method can be distributed by being stored in storage media such as magnetic disks (Floppy® disks, hard disks, and the like), optical disks (CD ROMs, DVDs, and the like), and semiconductor memories.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus comprising:

an X-ray tube holding device configured to generate X-rays;

an X-ray detector configured to detect the X-rays;

a rotator configured to hold the X-ray tube holding device so as to be rotatable about a first rotation axis obtained by setting an irradiation direction of the X-rays as an axis;

an arm configured to hold the rotator and the X-ray detector and rotatable about a second rotation axis different from the first rotation axis;

a tubular body configured to connect the X-ray tube holding device and a predetermined device away from the arm; and a control circuitry configured to control to rotate the rotator about the first rotation axis in the direction in which the torsion of the tubular body caused by the rotation of the arm is reduced, in accordance with the rotation of the arm about the second rotation axis, wherein the arm holds the rotator so as to be rotatable about the first rotation axis in a direction in which torsion of the tubular body is reduced.

2. The apparatus of claim 1, further comprising:

a holding mechanism configured to hold the arm so as to be rotatable about the second rotation axis, wherein the tubular body passes through the holding mechanism.

3. The apparatus of claim 2, wherein the second rotation axis is an axis passing through the holding mechanism and perpendicular to the first rotation axis when the arm is at an initial position.

4. The apparatus of claim 2, wherein the control circuitry controls to rotate the arm about the second rotation axis by not less than 360°.

5. The apparatus of claim 4, further comprising:

an image generation circuitry configured to generate a reconstruction image based on X-ray data at each angle, which has been detected by the X-ray detector during the rotation of the arm about the second rotation axis.

6. The apparatus of claim 4, further comprising:

an image generation circuitry configured to continuously generate fluoroscopic images based on a plurality of continuous X-ray data which have been detected by the X-ray detector during the rotation of the arm about the second rotation axis; and a display configured to continuously displays the fluoroscopic images.

7. The apparatus of claim 2, wherein the control circuitry controls to rotate the rotator about the first rotation axis in synchronism with the arm while the arm rotates about the second rotation axis.

8. The apparatus of claim 1, wherein the predetermined device is a high-voltage generator configured to generate a voltage to be applied to the X-ray tube holding device, and the tubular body is a high-voltage cable configured to connect the high-voltage generator and the X-ray tube holding device.

9. The apparatus of claim 1, wherein the X-ray tube holding device includes an X-ray tube configured to generate X-rays and a housing configured to store the X-ray tube, the predetermined device is a cooling device configured to circulate, in the housing, a medium for cooling the X-ray tube, and the tubular body is a hose configured to connect the cooling device and the housing.

10. The apparatus of claim 1, further comprising:

a top on which an object is to be placed; and a bed configured to support the top so as to be slidable in a longitudinal direction, wherein the bed moves along a body axis direction of the object while the arm continuously rotates about the second rotation axis by not less than 360°.

11. The apparatus of claim 1, further comprising:

a torsional relaxation mechanism provided between the X-ray tube holding device and the predetermined device and configured to relax torsion caused by the rotation of the tubular body by performing rotation in synchronism with the rotation of the X-ray tube holding device.

* * * * *